(12) United States Patent
Venturini et al.

(10) Patent No.: US 9,192,160 B2
(45) Date of Patent: Nov. 24, 2015

(54) AMINOINDANES AMIDES HAVING A HIGH FUNGICIDAL ACTIVITY AND THEIR PHYTOSANITARY COMPOSITIONS

(75) Inventors: Isabella Venturini, Cameri (IT); Matteo Santino Vazzola, Cogliate (IT); Entela Sinani, Novara (IT); Franco Pellacini, Milan (IT); Lucio Filippini, Novara (IT)

(73) Assignee: STICHTING I-F PRODUCT COLLABORATION, Amsterdam (NL)

( * ) Notice: Subject to any disclaimer, the term of this patent is extended or adjusted under 35 U.S.C. 154(b) by 42 days.

(21) Appl. No.: 13/995,853

(22) PCT Filed: Dec. 19, 2011

(86) PCT No.: PCT/EP2011/073225
§ 371 (c)(1),
(2), (4) Date: Sep. 10, 2013

(87) PCT Pub. No.: WO2012/084812
PCT Pub. Date: Jun. 28, 2012

(65) Prior Publication Data
US 2014/0011852 A1    Jan. 9, 2014

(30) Foreign Application Priority Data

Dec. 20, 2010 (IT) .............................. MI2010A2328

(51) Int. Cl.
| | |
|---|---|
| A01N 43/56 | (2006.01) |
| C07D 231/14 | (2006.01) |
| A01N 43/54 | (2006.01) |
| A01N 43/78 | (2006.01) |
| A01N 43/82 | (2006.01) |
| C07D 277/56 | (2006.01) |

(52) U.S. Cl.
CPC .............. *A01N 43/56* (2013.01); *A01N 43/54* (2013.01); *A01N 43/78* (2013.01); *A01N 43/82* (2013.01); *C07D 231/14* (2013.01); *C07D 277/56* (2013.01)

(58) Field of Classification Search
CPC ............................. A01N 43/56; C07D 231/14
USPC .................... 504/280, 266; 548/375.1, 374.1
See application file for complete search history.

(56) References Cited

U.S. PATENT DOCUMENTS

| | | | | |
|---|---|---|---|---|
| 4,742,074 A | * | 5/1988 | Nishida et al. ............. | 514/406 |
| 5,093,347 A | * | 3/1992 | Graneto et al. ............. | 514/406 |
| 7,470,793 B2 | * | 12/2008 | Dunkel et al. ............. | 548/181 |
| 2006/0155122 A1 | | 7/2006 | Dunkel | |
| 2010/0197925 A1 | | 8/2010 | Desbordes | |

FOREIGN PATENT DOCUMENTS

| | | |
|---|---|---|
| DE | 10250110 A1 | 5/2004 |
| EP | 0256503 A2 | 2/1988 |
| EP | 0276177 A1 | 7/1988 |
| EP | 0280275 A2 | 8/1988 |
| EP | 0569912 A1 | 11/1993 |
| JP | 6296471 A | 5/1987 |
| JP | 6470479 A | 3/1989 |
| JP | 01313402 A | 12/1989 |
| JP | 02157266 A | 6/1990 |
| JP | 2249966 A | 10/1990 |
| JP | 5310512 A | 11/1993 |
| JP | 01117864 A | 5/1999 |
| WO | 01/53259 A1 | 7/2001 |
| WO | 2004/018438 A1 | 3/2004 |
| WO | 2004/072023 A2 | 8/2004 |
| WO | 2004/103975 A1 | 12/2004 |
| WO | 2005/075452 A1 | 8/2005 |

OTHER PUBLICATIONS

Jeschke, P. Pest Manag. Sci. 2010, 66, 10-27, published on line Aug. 21, 2009.*
Erickson, JA et al., Hydrogen Donor Properties of the Difluoromethyl Group, J. Org. Chem. 1995, 60, 1626-1631.
Jerry March, Advanced Organic Chemistry, 1992, John Wiley & Sons, pp. 417-424; 392-402.
International Search Report in corresponding application PCT/EP2011/073225, dated Feb. 3, 2012.
English translation of Columbian Patent Office Action dated Dec. 16, 2014.

* cited by examiner

*Primary Examiner* — Sreeni Padmanabhan
*Assistant Examiner* — Irina Neagu
(74) *Attorney, Agent, or Firm* — Hedman & Costigan, P.C.; James V. Costigan; Kathleen A. Costigan

(57) ABSTRACT

New aminoindanes amides are described, having general formula (I)

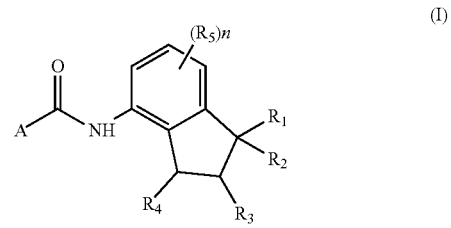

the relative phytosanitary compositions and their use for the control of phytopathogenic fungi.

16 Claims, No Drawings

AMINOINDANES AMIDES HAVING A HIGH FUNGICIDAL ACTIVITY AND THEIR PHYTOSANITARY COMPOSITIONS

The instant Application is a National Stage entry of International Application No. PCT/EP2011/073225, filed on 19 Dec. 2011, claiming the benefit of priority of Italy Patent Application No. MI2010 A002328, filed on 20 Dec. 2010.

The present invention relates to new amides of 4-aminoindanes having a high fungicidal activity, the relative phytosanitary compositions and their use for the control of phytopathogenic fungi.

More specifically, it relates to new amides of 4-aminoindanes, further substituted by specific groups on the phenyl group of indane, having a high activity in the control of pathogenic fungi of important agricultural crops.

Amides obtained from benzoic or hetero-cyclylcarboxylic acids condensed with 4-aminoindanes are described in patent applications JP1070479, JP 1117864, JP1313402, JP2157266, JP2249966, JP3077381, JP62096471, EP199822, EP256503, EP276177, EP280275, EP569912, U.S. Pat. No. 5,093,347, WO2001/53259, WO2004/018438, WO2004/039789, WO2004/072023, WO2004/103975, WO2005/075452.

In particular, EP199822 describes 1,3,5-trimethyl-N-(1,1-dimethyl-5-fluoro-4-indanyl)-4-pyrazolecarboxamide [compound (4)] and 1,5-dimethyl-3-trifluoro-methyl-N-(1,1-dimethyl-7-fluoro-4-indanyl)-4-pyrazolecarboxamide (page 15, lines 19-20); U.S. Pat. No. 5,093,347 describes 3-difluoromethyl-1-methyl-N-(1,1,3-trimethyl-4-indanyl)-4-pyrazolecarboxamide.

The amides of 4-aminoindanes described in the prior art, however, are not completely satisfactory from the point of view of the level of fungicidal activity against phytopathogenic fungi, the action range, and phytotoxicity with respect to the agricultural crops to be protected.

The Applicant has now surprisingly found that new amides, obtained by the condensation of heterocyclic acids substituted by a $CF_2H$ group, with 4-aminoindanes containing alkyl groups in positions 1 and 3 of indane and one or more further substituents on the phenyl ring, show, with respect to the compounds described above, a much higher fungicidal activity, a wider action range, a reduced or zero phytotoxicity with respect to the most important agricultural crops.

The object of the present invention therefore relates to aminoindanes amides having the structural formula (I):

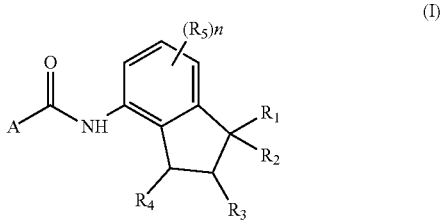

wherein:
$R_1$, $R_2$ and $R_4$, equal to or different from each other, represent a $C_1$-$C_2$ alkyl group, a $C_1$-$C_2$ haloalkyl group, a $C_3$-$C_6$ cycloalkyl group, a $C_3$-$C_6$ halocycloalkyl group, the groups $R_1$ and $R_2$ can also possibly be joined to form a $C_3$-$C_6$ cycloalkyl group spiro-condensed with indanyl;

$R_3$ represents a hydrogen atom, a $C_1$-$C_3$ alkyl group, a $C_1$-$C_3$ haloalkyl group, a $C_3$-$C_6$ cycloalkyl group, a $C_3$-$C_6$ halocycloalkyl group;
$R_5$ represents a halogen atom, a $C_1$-$C_4$ alkyl group, a $C_1$-$C_4$ haloalkyl group, a $C_1$-$C_4$ alkoxy group, a $C_1$-$C_4$ haloalkoxy group, an SH group, a $C_1$-$C_4$ alkylthio group, a $C_1$-$C_4$ haloalkylthio group;
n represents an integer ranging from 1 to 3;
A represents one of the following heterocycles $A_1$-$A_5$:

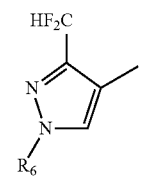

$A_1$

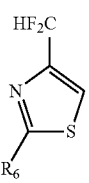

$A_2$

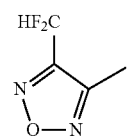

$A_3$

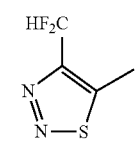

$A_4$

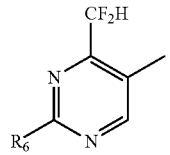

$A_5$ $R_6$ is a $C_1$-$C_3$ alkyl group, a $C_1$-$C_3$ haloalkyl group, a $C_3$-$C_6$ cycloalkyl group, a $C_3$-$C_6$ halocycloalkyl group, a $C_1$-$C_4$ alkoxy group, a $C_1$-$C_4$ haloalkoxy group, an SH group, a $C_1$-$C_4$ alkylthio group, a $C_1$-$C_4$ haloalkylthio group.

Examples of compounds having formula (I) which are particularly interesting for their activity are:
(1) 3-difluoromethyl-N-(7-fluoro-1,1,3-trimethyl-4-indanyl)-1-methyl-4-pyrazolecarboxamide;
(2) 4-difluoromethyl-N-(7-fluoro-1,1,3-trimethyl-4-indanyl)-2-methyl-5-thiazolecarboxamide;
(3) 3-difluoromethyl-1-methyl-N-(1,1,3,7-tetramethyl-4-indanyl)-pyrazolecarboxamide;
(4) 4-difluoromethyl-2-methyl-N-(1,1,3,7-tetramethyl-4-indanyl)-5-thiazolecarboxamide;
(5) 3-difluoromethyl-1-methyl-N-(7-methoxy-1,1,3-trimethyl-4-indanyl)-4-pyrazolecarboxamide;
(6) 4-difluoromethyl-2-methyl-N-(7-methoxy-1,1,3-trimethyl-4-indanyl)-5-thiazolecarboxamide;
(7) 3-difluoromethyl-1-methyl-N-(7-methylthio-1,1,3-trimethyl-4-indanyl)-4-pyrazolecarboxamide;
(8) 4-difluoromethyl-2-methyl-N-(7-methylthio-1,1,3-trimethyl-4-indanyl)-5-thiazolecarboxamide;

(9) 3-difluoromethyl-1-methyl-N-(7-trifluoromethoxy-1,1,3-trimethyl-4-indanyl)-4-pyrazolecarboxamide;

(10) 4-difluoromethyl-2-methyl-N-(7-trifluoromethoxy-1,1,3-trimethyl-4-indanyl)-5-thiazolecarboxamide;

(11) 3-difluoromethyl-N-(7-fluoro-1,1,3-trimethyl-4-indanyl)-4-furazancarboxamide

(12) 4-difluoromethyl-N-(7-fluoro-1,1,3-trimethyl-4-indanyl)-2-methylthio-5-pyrimidinecarboxamide.

(13) 3-difluoromethyl-N-(7-chloro-1,1,3-trimethyl-4-indanyl)-1-methyl-4-pyrazolecarboxamide;

(14) 3-difluoromethyl-N-(7-chloro-1,1-diethyl-3-methyl-4-indanyl)-1-methyl-4-pyrazolecarboxamide;

(15) 4-difluoromethyl-N-(7-fluoro-1,1,3-trimethyl-4-indanyl)-5-thiadiazolecarboxamide.

Preferred compounds having general formula (I) are those wherein A represents $A_1$, $R_1$, $R_2$, $R_4$ and $R_6$ are a methyl group, $R_3$ is a hydrogen atom, $R_5$ represents a halogen.

Examples of halogen are: fluorine, chlorine, bromine, iodine.

Examples of $C_1$-$C_4$ alkyl, linear or branched, are methyl, ethyl, n-propyl, isopropyl, n-butyl, isobutyl, sec-butyl, tert-butyl.

Examples of $C_1$-$C_4$ haloalkyl are fluoromethyl, difluoromethyl, trifluoromethyl, chloromethyl, dichloromethyl, 2,2,2-trifluoroethyl, 1,1,2,2-tetrafluoroethyl, pentafluoroethyl, heptafluoropropyl, 4,4,4-trichlorobutyl.

Examples of $C_1$-$C_4$ alkoxy, linear or branched, are methoxy, ethoxy, n-propoxy, isopropoxy, n-butoxy, isobutoxy, sec-butoxy, tert-butoxy.

Examples of $C_1$-$C_4$ haloalkoxy are fluoromethoxy, difluoromethoxy, trifluoromethoxy, chloromethoxy, dichloromethoxy, 2,2,2-trifluoroethoxy, 1,1,2,2-tetra-fluoroethoxy, 1,1,2,3,3,3-hexafluoropropoxy, 4,4,4-trichlorobutoxy.

Examples of $C_3$-$C_6$ cycloalkyl are cyclopropyl, cyclobutyl, cyclopentyl, cyclohexyl.

Examples of $C_3$-$C_6$ halocycloalkyl are 2,2-dichloro-cyclopropyl, 2,2-difluorocyclopropyl, 2,2,3,3-tetrafluorocyclobutyl, 3,3-difluorocyclopentyl, 2-fluorocyclohexyl.

Examples of $C_1$-$C_4$ alkylthio, linear or branched, are methylthio, ethylthio, n-propylthio, isopropylthio, n-butylthio, isobutylthio, sec-butylthio, tert-butylthio.

Examples of $C_1$-$C_4$ haloalkylthio are fluoromethylthio, difluoromethylthio, trifluoromethyl-thio, chloromethylthio, dichloromethylthio, 2,2,2-trifluoroethylthio, 1,1,2,2-tetrafluoroethylthio, 1,1,2,3,3,3-hexafluoropropyl-thio, 4,4,4-trichloro-butylthio.

Due to the asymmetry of the carbon atom in position 3 of the indanyl ring and possibly the atoms in position 1 (when $R_1$ is different from $R_2$) and 2 (when $R_3$ is different from hydrogen), the compounds having formula (I) may occur as mixtures of optical isomers and possibly diastereoisomers.

The compounds having formula (I) are therefore included in the spirit of the present invention both as racemic and possibly diastereoisomeric mixtures, both as partially separated mixtures, either as single optical isomers and possibly as single diastereoisomers.

The compounds having formula (I) are prepared by reacting a substituted acid or one of its derivatives having formula (II), with an aniline having formula (III), according to the reaction scheme indicated below:

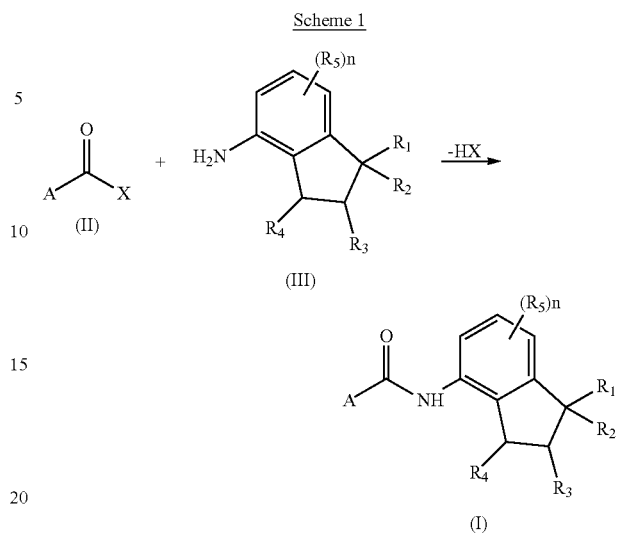

Scheme 1

In these formulae:
A, $R_1$, $R_2$, $R_3$, $R_4$, $R_5$ and n have the meanings defined above;
X represents a hydroxy OH; a halogen atom; a $C_1$-$C_4$ alkoxy group; a phenoxy group; an acyloxy group RCOO wherein R in turn represents a group A, a $C_1$-$C_4$ alkyl group or a phenyl optionally substituted by $C_1$-$C_4$ alkyl groups, $C_1$-$C_4$ haloalky groups, halogen atoms.

The reaction conditions for effecting the process indicated above, in which an acid or one of its corresponding halides, esters or anhydrides (possibly mixed) is reacted with an amine, are widely described in chemical literature, for example in "Advanced Organic Chemistry", Jerry March, $4^{th}$ Edition, 1992, John Wiley & Sons Pub., pages 417-424 and references cited therein.

Various alternative conditions can be selected, also depending on the nature of the compound having formula (II); for example, when X represents a halogen atom, preferably chlorine, the reaction is normally carried out in the presence of an inert solvent and in the presence of an organic or inorganic base, at a temperature ranging from −20° C. to the boiling point of the reaction mixture.

Examples of solvents which can be used for the above reaction include water, aliphatic or cycloaliphatic hydrocarbons (petroleum ether, hexane, cyclohexane etc.), chlorinated hydrocarbons (methylene chloride, chloroform, carbon tetrachloride, dichloroethane, etc.), aromatic hydrocarbons (benzene, toluene, xylene, chlorobenzene, etc.), ethers (diethyl ether, diisopropyl ether, dimethoxyethane, dioxane, tetrahydrofuran, etc.), esters (ethyl acetate etc.), ketones (acetone, methylethylketone, methylpropyl-ketone, methylisobutylketone, etc.), nitriles (acetonitrile, benzonitrile, etc.), aprotic dipolar solvents (dimethylformamide, dimethylacetamide, hexamethylphosphorotriamide, dimethylsulfoxide, sulfolane, N-methylpyrrolidone, etc.)

Inorganic bases which can be used for the purpose are, for example, hydroxides, carbonates and bicarbonates of sodium or potassium.

Organic bases which can be used for the purpose are, for example, triethylamine, pyridine, 4-N,N-dimethyl-aminopyridine, N,N-dimethylaniline, N-methyl-piperidine, lutidine, diazabicyclo-octane (DABCO), diazabicyclononene (DBN), diazabicycloundecene (DBU).

The intermediates having general formulae (II) and (III), when they are not already described in literature, can in any case be prepared by adapting synthetic methods well known to experts in the field.

For example, pyrazolecarboxylic acids [formula (II) wherein $A=A_1$, $X=OH$] can be prepared according to what is described in U.S. Pat. No. 5,093,347; thiazolecarboxylic acids [formula (II) wherein $A=A_2$, $X=OH$] can be prepared according to what is described in DE 10250110; pyrimidinecarboxylic acids [formula (II) wherein $A=A_4$, $X=OH$] can be prepared according to what is described in EP 569912.

The corresponding acid derivatives (esters, anhydrides, halides) can be easily prepared from these according to what is described, for example, in "Advanced Organic Chemistry", Jerry March, $4^{th}$ Edition, 1992, John Wiley & Sons Pub., pages 392-402, 437-438 and references cited therein.

As already mentioned, the compounds having general formula (I) have a very high fungicidal activity which is exerted with respect to numerous phytopathogenic fungi which attack important agricultural crops.

A further object of the present invention therefore relates to the use of the compounds having general formula (I) for the control of phytopathogenic fungi of agricultural crops.

Examples of phytopathogenic fungi which can be effectively fought with the compounds of general formula (I) according to the present invention, are those belonging to the groups of Basidiomycetes, Ascomycetes, Deuteromycetes or fungi imperfecti, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides*, *Colletotrichum* spp., *Pyricularia oryzae*, *Sclerotium* spp., *Phytophtora* spp., *Pythium* spp., *Plasmopara viticola*, *Peronospora* spp., *Pseudoperonospora cubensis*, *Bremia lactucae*.

The main crops which can be protected with the compounds of the present invention comprise cereals (wheat, barley, rye, oats, rice, corn, sorghum, etc.), fruit trees (apple, pear, plumb, peach, almond, cherry, banana, vines, strawberry, raspberry, blackberry, etc.), citrus trees (orange, lemon, mandarin, grapefruit, etc.), legumes (beans, peas, lentils, soybean, etc.), vegetables (spinach, lettuce, asparagus, cabbage, carrots, onions, tomatoes, potatoes, aubergines, peppers, etc.), cucurbitaceae (pumpkins, zucchini, cucumbers, melons, water-melons, etc.), oilseeds (sunflower, rape, peanut, castor-oil plant, coconut, etc.) tobacco, coffee, tea, cocoa, sugar beet, sugar cane, cotton.

In particular, the compounds having general formula (I) have proved to be considerably effective in the control of *Plasmopara viticola* on vines, *Phytophtora infestans* and *Botrytis Cinerea* on tomatoes, *Puccinia recondita*, *Erysiphe graminis*, *Helminthosporium teres*, *Septoria nodorum* and *Fusarium* spp. on cereals; in the control of *Phakopsora pachyrhizi* on soya; in the control of *Uromyces appendiculatus* on beans; in the control of *Venturia inaequalis* on apples, in the control of *Sphaeroteca fuliginea* on cucumbers.

Furthermore, the compounds having general formula (I) are also effective in the control of phytopathogenic bacteria and viruses, such as for example *Xanthomonas* spp., *Pseudomonas* spp., *Erwinia amylovora*, the mosaic virus of tobacco.

The compounds having formula (I) are capable of exerting a fungicidal action of both in curative and preventive applications and have a very low or zero phytotoxicity on the crops treated.

For practical uses in agriculture, it is often preferable to use fungicidal compositions containing compounds having formula (I) according to the present invention, suitably formulated.

A further object of the present invention relates to fungicidal compositions comprising one or more compounds having formula (I), a solvent and/or solid or liquid diluent, possibly a surfactant.

The above fungicidal compositions can be in the form of dry powders, wettable powders, emulsifiable concentrates, emulsions, micro-emulsions, pastes, granulates, water dispersible granules, solutions, suspensions, etc.: the choice of the type of composition will depend on the specific use.

The fungicidal compositions are prepared in the known way, for example by diluting or dissolving the active substance with a solvent medium and/or a solid or liquid diluent, possibly in the presence of surfactants.

Solid diluents or supports which can be used for example are: silica, kaolin, bentonite, talc, diatomaceous earth, dolomite, calcium carbonate, magnesia, gypsum, clays, synthetic silicates, attapulgite, sepiolite.

Solvents or liquid diluents which can be used, are for example, in addition to water, aromatic organic solvents (xylols or blends of alkylbenzols, chlorobenzene, etc.), paraffins (petroleum fractions), alcohols (methanol, propanol, butanol, octanol, glycerine, etc.), esters (ethyl acetate, isobutyl acetate, alkyl carbonates, alkyl esters of adipic acid, alkyl esters of glutaric acid, alkyl esters of succinic acid, alkyl esters of lactic acid, etc.), vegetable oils (rape oil, sunflower oil, soybean oil, castor oil, corn oil, peanut oil, and their alkyl esters), ketones (cyclohexanone, acetone, acetophenone, isophorone, ethylamylketone, etc.), amides (N,N-dimethylformamide, N-methylpyrrolidone, etc.), sulfoxides and sulfones (dimethylsulfoxide, dimethylsulfone, etc.), and mixtures thereof.

Sodium salts, calcium salts, potassium salts, salts of triethylamine or triethanolamine of alkyl-naphthalenesulfonates, polynaphthalenesulfonates, alkyl sulfonates, aryl sulfonates, alkylaryl sulfonates, polycarboxylates, sulfosuccinates, alkyl sulfosuccinates, lignin sulfonates, alkyl sulfates, can be used as surfactants; as also polyethoxylated fatty alcohols, polyethoxylated alkylphenols, polyethoxylated esters of sorbitol, polypropoxy polyethoxylates (block polymers).

The fungicidal compositions can also contain special additives for particular purposes, such as for example, antifreeze agents such as propylene glycol, or adhesion agents, such as gum Arabic, polyvinyl alcohol, polyvinyl pyrrolidone, etc.

If desired, other compatible active principles can be added to the fungicidal compositions containing the compounds of general formula (I), such as, for example, fungicides different from those having general formula (I), phytoregulators, antibiotics, herbicides, insecticides, fertilizers and/or mixtures thereof.

Examples of fungicides different from those having general formula (I), which can be included in the fungicidal compositions object of the present invention are: acibenzolar, ametoctradin, amisulbrom, ampropylfos, anilazine, azaconazole, azoxystrobin, benalaxyl, benalaxyl-M, benomyl, benthiavalicarb, bitertanol, bixafen, blasticidin-S, boscalid, bromuconazole, bupirimate, buthiobate, captafol, captan, carbendazim, carboxin, carpropamid, chinomethionat, chloroneb, chlorothalonil, chlozolinate, cyazofamid, cyflufenamid, cymoxanil, cyproconazole, cyprodinil, debacarb, dichlofluanid, dichlone, diclobutrazol, diclomezine, dicloran, diclocymet, diethofencarb, difenoconazole, diflumetorim, dimethirimol, dimethomorph, dimoxystrobin, diniconazole, dinocap, dipyrithione, ditalimfos, dithianon, dodemorph, dodine, edifenphos, epoxiconazole, etaconazole, ethaboxam, ethirimol, ethoxyquin, etridiazole, famoxadone, fenamidone, fenaminosulf, fenapanil, fenarimol, fenbuconazole, fenfuram, fenhexamid, fenoxanil, fenpiclonil, fenpropidin, fenpropimorph, fentin, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, folpet, fosetyl-aluminium, fuberidazole, furalaxyl, furametpyr, furconazole, furconazole-cis, guazatine, hexaconazole, hymexazol, idrossichinolina solfato, imazalil, imibenconazole, iminoctadine, ipconazole, iprobenfos, iprodione, isoprothiolane, iprovalicarb, isopyrazam, isotianil, kasugamycin, kresoximmethyl, mancopper, mancozeb, mandipropamid, maneb, mebenil, mepanipyrim, mepronil, meptyldinocap, metalaxyl, metalaxyl-M, metconazole, methfuroxam, metiram, metominostrobin, metrafenone, metsulfovax, myclobutanil, natamycin, nicobifen, nitrothal-isopropyl, nuarimol, ofurace, orysastrobin, oxadixyl, oxpoconazole, oxycarboxin, pefurazoate, penconazole, pencycuron, penflufen, pentachlorofenol and its salts, penthiopyrad, phthalide, picoxystrobin, piperalin, Bordeaux mixture, polyoxins, probenazole, prochloraz, procymidone, propamocarb, propiconazole, propineb, proquinazid, prothiocarb, prothioconazole, pyracarbolid, pyraclostrobin, pyrametostrobin, pyraoxystrobin, pyrazophos, pyribencarb, pyrifenox, pyrimethanil, pyroquilon, pyroxyfur, quinacetol, quinazamid, quinconazole, quinoxyfen, quintozene, rabenzazole, copper hydroxide, copper oxychloride, copper (I) oxide, copper sulfate, sedaxane, silthiofam, simeconazole, spiroxamine, streptomycin, tebuconazole, tetraconazole, thiabendazole, thiadifluor, thicyofen, thifluzamide, thiophanate, thiophanate-methyl, thiram, tiadinil, tioxymid, tolclofos-methyl, tolylfluanid, triadimefon, triadimenol, triarimol, triazbutil, triazoxide, tricyclazole, tridemorf, trifloxystrobin, triflumizole, triforine, triticonazole, uniconazole, uniconazole-P, validamycin, valifenalate, vinclozolin, zineb, ziram, sulfur, zoxamide.

The concentration of compounds having general formula (I) in the above compositions can vary within a wide range; it generally ranges from 1% to 90%, preferably from 5% to 50%.

The application of these compositions can be effected on each part of the plant, for example on the leaves, stems, branches and roots, or on the seeds themselves before sowing, or on the ground in which the plant grows.

A further object of the present invention therefore relates to a method for the control of phytopathogenic fungi in agricultural crops, which consists in the application of effective dosages of the compounds having formula (I), used as such or formulated in fungicidal compositions as described above.

The quantity of compound to be applied for obtaining the desired effect can vary in relation to different factors, such as, for example, the compound used, the crop to be preserved, the type of pathogen, the degree of infection, the climatic conditions, the application method, the formulation adopted.

Doses of compound ranging from 10 g to 5 kg per hectare of agricultural crop generally provide a sufficient control.

The following examples are provided for a better understanding of the invention for illustrative and non-limiting purposes of the same.

EXAMPLE 1

Preparation of 3-difluoromethyl-N-(7-fluoro-1,1,3-trimethyl-4-indanyl)-1-methyl-4-pyrazolecarboxamide (Compound N. 1)

0.4 ml of triethylamine were dropped into a solution of 7-fluoro-1,1,3-trimethyl-4-aminoindane (0.45 g) and 3-(difluoromethyl)-1-methyl-1H-pyrazole-4-carbonyl chloride (0.44 g) in 8 ml of dichloromethane.

After being kept under stirring for 8 hours at room temperature, diluted hydrochloric acid was added to the reaction mixture, the phases were separated and the aqueous phase was extracted with dichloromethane.

The organic phases were then joined, anhydrified with sodium sulfate and concentrated at reduced pressure.

The raw product obtained was subsequently purified on a silica gel column (eluent hexane/ethyl acetate 8/2) to give 0.45 g of the desired product, a white solid with a melting point of 147° C.

$^1$H NMR (200 Mhz, CDCl$_3$) δ a: 1.43 (3H, d), 1.38 (3H, s), 1.44 (3H, s), 1.66 (1H, dd), 2.21 (1H, dd), 3.38 (1H m), 3.98 (3H, s), 6.81 (1H, bs), 6.95 (1H, t), 6.70 (1H, m), 7.81 (1H, bs), 8.03 (1H, bs).

EXAMPLE 2

Preparation of Compounds N.2-8.

Analogously to the procedure of Example 1, the compounds of general formula (I) reported in Table 1 have been prepared.

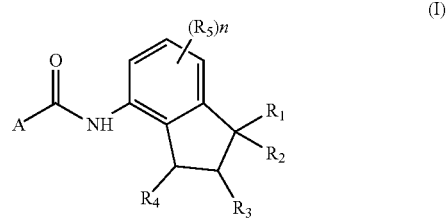

(I)

TABLE 1

| Compound N° | A | R$_1$ | R$_2$ | R$_3$ | R$_4$ | R$_5$ |
|---|---|---|---|---|---|---|
| 2 | 3-difluoromethyl-1-methyl-4-pyrazolyl | Et | Et | H | Me | 7-F |
| 3 | 3-difluoromethyl-1-methyl-4-pyrazolyl | Me | Me | H | Me | 7-OMe |
| 4 | 4-difluoromethyl-2-methyl-5-thiazolyl | Me | Me | H | Me | 7-F |
| 5 | 3-difluoromethyl-1-methyl-4-pyrazolyl | Me | Me | H | Me | 7-Me |
| 6 | 3-difluoromethyl-1-methyl-4-pyrazolyl | Me | Me | H | Me | 7-Cl |
| 7 | 3-difluoromethyl-1-methyl-4-pyrazolyl | Me | Me | H | Me | 7-OCF$_3$ |
| 8 | 3-difluoromethyl-1-methyl-4-pyrazolyl | Me | Me | H | Me | 7-SMe |

Melting points:
N° 2: 115° C.;
N° 3: 110° C.;
N° 4: 95° C.;
N° 6: 140° C.;
N° 7: 105° C.;
N° 8: 97° C.

EXAMPLE 3

Determination of the Fungicidal Activity in Preventive application (5 Days) against *Erysiphe graminis* on Wheat Leaves of wheat plants of the Salgemma variety, grown in pots in a conditioned environment kept at 20° C. and 70% of relative humidity (R.H.), were treated by spraying on both sides of the leaves with the compounds under examination, dispersed in hydroacetonic solutions at 20% by volume of acetone.

After remaining 5 days in a conditioned environment, the plants were infected under dry conditions by shaking over them, in order to distribute the inoculum, plants previously infected by Erysiphe graminis.

The plants were then maintained in the same cell, in a humidity-saturated environment and at a temperature ranging from 18 to 24° C. for 12 days.

At the end of this period, the external symptoms of the pathogen appeared and it was therefore possible to proceed with the evaluation of the intensity of the infection, on both the parts treated directly with the products (T), and also on the parts which had developed during the test (NT), by means of a visible percentage evaluation scale of the area of affected leafs; the scale comprises, as extremes, the value 100 (healthy plant) and the value 0 (completely infected plant).

At the same time, the phytotoxicity was evaluated (percentage of leaf necrosis) induced on the wheat plants by the application of the products: in this case, the evaluation scale varies from 0 (completely healthy plant) to 100 (completely necrotized plant).

Table 2 shows the results obtained by carrying out the test described with compound N. 1, compared with the following reference products described in prior art:

RC1: 3-difluoromethyl-1-methyl-N-(1,1,3-trimethyl-4-indanyl)-4-pyrazolecarboxamide of U.S. Pat. No. 5,093,347;
RC2: 1,5-dimethyl-3-trifluoro-methyl-N-(1,1-dimethyl-7-fluoro-4-indanyl)-4-pyrazolecarboxamide [EP199822, page 15, lines 19-20];
RC3: 1,3,5-trimethyl-N-(1,1-dimethyl-5-fluoro-4-indanyl)-4-pyrazolecarboxamide [EP199822, compound (4)].

TABLE 2

| | Preventive fungicidal activity (5 days) against Erysiphe graminis on wheat. | | |
|---|---|---|---|
| Compound | Dose (ppm) | Activity T/NT | Phytotoxicity |
| N. 1 | 125 | 95/90 | 0 |
| CR-1 | 125 | 70/65 | 10 |
| CR-2 | 125 | 25/15 | 0 |
| CR-3 | 125 | 10/0 | 0 |

The invention claimed is:

1. Aminoindane amides having structural formula (I) or isomers thereof:

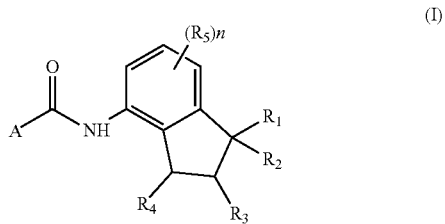

wherein:
$R_1$, $R_2$ and $R_4$, equal to or different from each other, represent a $C_1$-$C_3$ alkyl group;
$R_3$ represents a hydrogen atom, a $C_1$-$C_3$ alkyl group, a $C_1$-$C_3$ haloalkyl group, a $C_3$-$C_6$ cycloalkyl group, a $C_3$-$C_6$ halocycloalkyl group;
$R_5$ represents a halogen atom, a $C_1$-$C_4$ haloalkyl group, a $C_1$-$C_4$ alkoxy group, a $C_1$-$C_4$ haloalkoxy group, a $C_1$-$C_4$ alkylthio group;
n represents an integer ranging from 1 to 3;
A represents the following heterocycle:

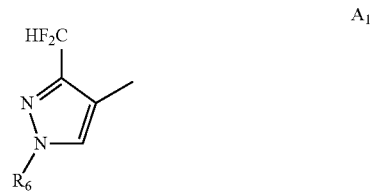

wherein the unconnected bond in said heterocycle represents a molecular bond to the carboxmide group of structure of formula (I);
$R_6$ is a $C_1$-$C_3$ alkyl group, a $C_1$-$C_3$ haloalkyl group, a $C_3$-$C_6$ cycloalkyl group, a $C_3$-$C_6$ halocycloalkyl group, a $C_1$-$C_4$ alkoxy group, a $C_1$-$C_4$ haloalkoxy group, an SH group, a $C_1$-$C_4$ alkylthio group, a $C_1$-$C_4$ haloalkylthio group.

2. The compounds according to claim 1, characterized in that in formula (I), A represents $A_1$, $R_1$, $R_2$, $R_4$ and $R_6$ are a methyl group, $R_3$ is a hydrogen atom, $R_5$ represents a halogen.

3. The compounds according to claim 1, selected from the following compounds having general formula (I):
3-difluoromethyl-N-(7-fluoro-1,1,3-trimethyl-4-indanyl)-1-methyl-4-pyrazolecarboxamide;
3-difluoromethyl-1-methyl-N-(7-methoxy-1,1,3-trimethyl-4-indanyl)-4-pyrazolecarboxamide;
3-difluoromethyl-1-methyl-N-(7-trifluoromethoxy-1,1,3-trimethyl-4-indanyl)-4-pyrazolecarboxamide;
3-difluoromethyl-1-methyl-N-(7-methylthio-1,1,3-trimethyl-4-indanyl)-4-pyrazolecarboxamide;
3-difluoromethyl-N-(7-chloro-1,1,3-trimethyl-4-indanyl)-1-methyl-4-pyrazolecarboxamide.

4. The compounds according to claim 1, characterized in that they are in the form of racemic mixtures, diastereoisomeric mixtures, partially separated mixtures, single optical isomers and/or single diastereoisomers.

5. Fungicidal compositions comprising one or more compounds having formula (I) according to claim 1, a solvent and/or solid or liquid diluent and a surfactant.

6. The compositions according to claim 5, wherein the concentration of compounds having general formula (I) ranges from 1 to 90% by weight with respect to the total weight of the composition, preferably from 5 to 50% by weight with respect to the total weight of the composition.

7. A method for the control of phytopathogenic fungi of agricultural crops which comprises applying to an agricultural crop an effective amount of an aminoindane amide having structural formula (I):

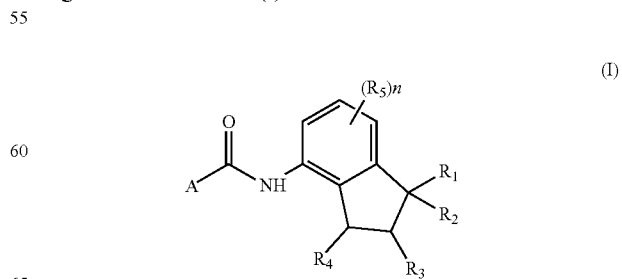

wherein:

$R_1$, $R_2$ and $R_4$, equal to or different from each other, represent a $C_1$-$C_3$ alkyl group;

$R_3$ represents a hydrogen atom, a $C_1$-$C_3$ alkyl group, a $C_1$-$C_3$ haloalkyl group, a $C_3$-$C_6$ cycloalkyl group, a $C_3$-$C_6$ halocycloalkyl group;

$R_5$ represents a halogen atom, a $C_1$-$C_4$ haloalkyl group, a $C_1$-$C_4$ alkoxy group, a $C_1$-$C_4$ haloalkoxy group, a $C_1$-$C_4$ alkylthio group;

n represents an integer ranging from 1 to 3;

A represents the following heterocycle:

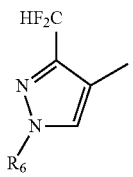

A₁ wherein the unconnected bond in said heterocycle represents a molecular bond to the carboxamide group of structure of formula (I);

$R_6$ is a $C_1$-$C_3$ alkyl group, a $C_1$-$C_3$ haloalkyl group, a $C_3$-$C_6$ cycloalkyl group, a $C_3$-$C_6$ halocycloalkyl group, a $C_1$-$C_4$ alkoxy group, a $C_1$-$C_4$ haloalkoxy group, an SH group, a $C_1$-$C_4$ alkylthio group, a $C_1$-$C_4$ haloalkylthio group, for the control of phytopathogenic fungi of agricultural crops.

8. A method for the control of phytopathogenic fungi of agricultural crops which comprises applying to an agricultural crop an effective amount of a compounds according to claim 2.

9. A method for the control of phytopathogenic fungi of agricultural crops which comprises applying to agricultural crops an effective amount of a composition according to claim 5.

10. The method of claim 7, for the control of phytopathogenic fungi belonging to the group of *Basidiomycetes, Ascomycetes, Deuteromycetes* or fungi imperfecti, *Oomycetes*: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophtora* spp., *Pythium* spp., *Plasmopara viticola, Peronospora* spp., *Pseudoperonospora cubensis,* and *Bremia lactucae.*

11. The method of claim 7, wherein the agricultural crops are cereals, fruit trees, citrus fruits, legumes, horticultural crops, cucurbits, oleaginous plants, tobacco, coffee, tea, cocoa, sugar beet, sugar cane, cotton.

12. The method of claim 7 for the control of *Plasmopara viticola* on vines, *Phytophtora infestans* and *Botrytis Cinerea* on tomatoes, *Puccinia recondita, Erisiphae graminis, Helminthosporium teres, Septoria nodorum* and *Fusarium* spp. on cereals; *Phakopsora pachyrhizi* on soya; *Uromyces appendiculatus* on beans; *Venturia inaequalis* on apples, *Sphaeroteca fuliginea* on cucumbers.

13. A method for the control of phytopathogenic fungi of agricultural crops which comprises applying to an agricultural crop an effective amount of a compound according to claim 1 for the control of phytopathogenic bacteria or viruses.

14. A method for controlling phytopathogenic fungi in agricultural crops, which consists in applying effective doses of compounds according to claim 1 in amounts ranging from 10 g to 5 kg of compound having formula (I) per hectare of agricultural crop.

15. A method for the control of phytopathogenic fungi of agricultural crops which comprises applying to an agricultural crop an effective amount of a composition according to claim 5 for the control of phytopathogenic bacteria or viruses.

16. A method for controlling phytopathogenic fungi in agricultural crops, which consists in applying effective doses of fungicidal compositions according to claim 5, in amounts ranging from 10 g to 5 kg of compound having formula (I) per hectare of agricultural crop.

\* \* \* \* \*